(12) United States Patent
Farris et al.

(10) Patent No.: US 6,514,266 B2
(45) Date of Patent: Feb. 4, 2003

(54) METHOD AND DEVICE FOR IMPROVED CORNEAL SECTIONS

(75) Inventors: Michael R. Farris, Windermere, FL (US); William I. Kern, Longwood, FL (US); Lewis Harrold, Winter Springs, FL (US)

(73) Assignee: LaserSight Technologies, Inc., Winter Park, FL (US)

(*) Notice: Subject to any disclaimer, the term of this patent is extended or adjusted under 35 U.S.C. 154(b) by 0 days.

(21) Appl. No.: 09/764,354

(22) Filed: Jan. 19, 2001

(65) Prior Publication Data

US 2001/0037122 A1 Nov. 1, 2001

Related U.S. Application Data

(60) Provisional application No. 60/179,021, filed on Jan. 31, 2000.

(51) Int. Cl.$^7$ ................................................. A61F 9/00
(52) U.S. Cl. ........................................................ 606/166
(58) Field of Search ................................ 606/4–6, 131, 606/166, 167, 132, 170, 172; 30/346, 350

(56) References Cited

U.S. PATENT DOCUMENTS

| | | | | |
|---|---|---|---|---|
| 4,665,914 A | * | 5/1987 | Tanne | |
| 5,411,511 A | * | 5/1995 | Hall | |
| 5,437,657 A | * | 8/1995 | Epstein | |
| 5,586,980 A | * | 12/1996 | Kremer et al. | 606/4 |
| 5,591,174 A | * | 1/1997 | Clark et al. | |
| 5,997,559 A | * | 12/1999 | Zeimer | |
| 6,126,668 A | * | 10/2000 | Bair et al. | |

* cited by examiner

*Primary Examiner*—Marvin M. Lateef
*Assistant Examiner*—Ali M. Imam
(74) *Attorney, Agent, or Firm*—William H. Bollman

(57) ABSTRACT

A keratome includes a head assembly having a cutting head and blade for cutting corneal tissue and an applanation member associated with the cutting head. The keratome includes an eyeball retaining structure and at least one sensor is associated with the keratome providing measurement of a respective at least one operative factor during cutting of the corneal tissue.

17 Claims, 3 Drawing Sheets

METHOD AND DEVICE FOR IMPROVED CORNEAL SECTIONS

This application is based on and claims priority from U.S. Provisional Application Ser. No. 60/179,021, filed on Jan. 31, 2000.

BACKGROUND OF THE INVENTION

1. Field of the Invention

The present invention relates generally to a keratome and method of cutting corneal tissue and more particularly to a keratome and method of intraoperatively controlling an operating parameter of the keratome to improve cutting of the corneal tissue.

2. Background

Corneal refractive surgery utilizes an instrument commonly known as a keratome for producing full or partial sections on both the anterior surface of the cornea and within the stromal structure when exposed by a superficial section. The keratome is a mechanical device for performing lamellar resections. The refractive procedures performed with the conventional keratome include AK, ALK, and LASIK. Keratome instruments are available with manual operation, in which case only blade oscillation is motor driven and the cutting head of the instrument is traversed across the corneal surface by the surgeon's hand. The keratome is also available with more automatic operation. The automatic keratome incorporates a drive mechanism that, in addition to providing blade oscillation, provides transverse movement of the cutting head across the corneal surface.

While the state-of-the art for keratomes has produced instruments with improved clinical performance, none of the currently available keratome instruments, or the improvements incorporated therein, have addressed improving intra-operative performance and results by monitoring one, or more, of the factors influencing clinical outcomes. These factors can include changes in intraocular pressure which alter tissue stiffness and forces on the blade, the pressure applied by the eyeball holding ring on the corneal surface, speed and uniformity of translation of the keratome's cutting head, keratome blade oscillation speed, tissue compression, blade motion outside of a defined envelope, blade slowdown, motion in mechanical structure that alters blade position, travel velocity which alters the fluid dynamics of the tissue moving past the blade and across the cutter surfaces, and other factors related to forces applied to the cornea during the cutting cycle.

Accordingly, there is a need to control operating parameters of an automated keratome based on measuring operative factors during the procedure.

SUMMARY OF THE INVENTION

An object of the invention is to fulfill the need referred to above. In accordance with the principles of the present invention, this objective is achieved by providing a keratome including a head assembly having a cutting head and blade for cutting corneal tissue and an applanation member associated with the cutting head. The keratome includes an eyeball retaining structure and at least one sensor is associated with the keratome providing measurement of a respective at least one operative factor during cutting of the corneal tissue.

In accordance with another aspect of the invention, a method of controlling cutting of corneal tissue with a blade of a keratome during operation includes measuring an operative factor of a keratome during operation of the keratome, and controlling in real time a movement of the blade based on the measured operative factor.

Other objects, features and characteristics of the present invention, as well as the methods of operation and the functions of the related elements of the structure, the combination of parts and economics of manufacture will become more apparent upon consideration of the following detailed description and appended claims with reference to the accompanying drawings, all of which form a part of this specification.

DETAILED DESCRIPTION OF ILLUSTRATIVE EMBODIMENTS

Figure 1:
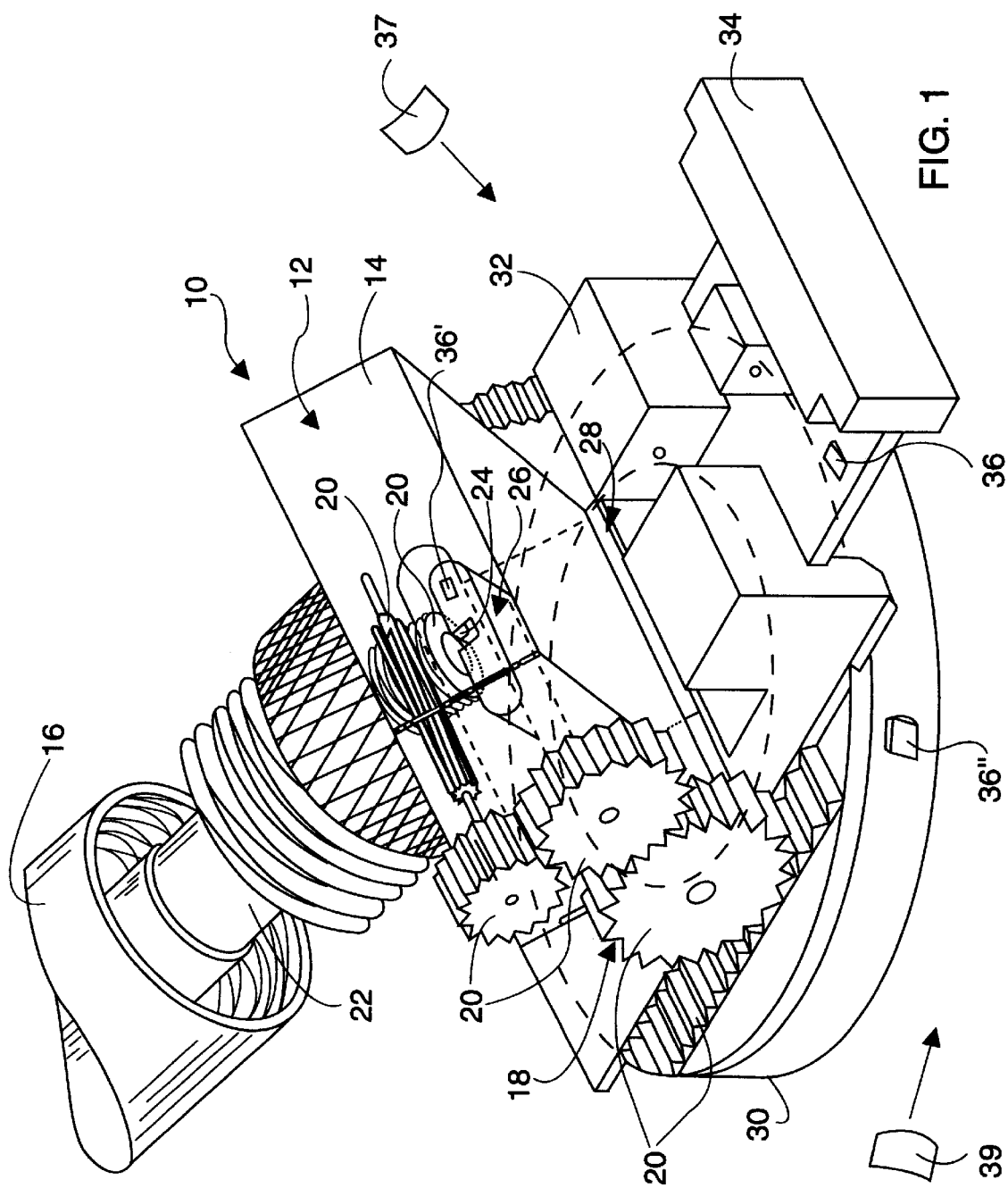
FIG. 1 is a perspective view of a keratome provided in accordance with the principles of the present invention.

With reference to FIG. 1, a keratome, generally indicated at 10, is provided in accordance with the principles of the present invention. The keratome 10 may be, for example, of the type described in U.S. Pat. No. 35,421, entitled "Automated Corneal Shaper", the contents of which are hereby incorporated into the present specification by reference. The keratome 10 includes a head assembly, generally indicated at 12, including a cutting head 14, and drive structure. The drive structure comprises at least one motor 16 and a drive mechanism 18 operatively associated with the cutting head 14 and motor 16 to drive the cutting head 14. In the illustrated embodiment, the drive structure comprises a plurality of intermeshing gears 20 operatively associated with a shaft 22 which is driven by the motor 16. The gears 20 are constructed and arranged to convert rotation of the shaft 22 to translation of the cutting head 14.

In addition, an eccentric 24 imparts oscillating motion to a blade holder 26 of the cutting head 14 as the eccentric 24 revolves with the shaft 22. A blade 28 for cutting corneal tissue is coupled to the blade holder 26, which in turn is inserted into the cutting head 14. Alternatively, a separately controllable motor 29 may be operatively associated with the blade holder 26 to control blade oscillation instead of using the single motor 16 to cause translation and oscillation of the blade 28. Thus, the blade 28 is caused to oscillate transversely, preferably at a constant rate. The motors 16 and 29 can be considered part of the keratome or may be separate therefrom.

A eyeball retaining ring 30 functions to fix the eye in position and to provide a fixed support along which the cutting head 14 will slide to resect the corneal tissue with the blade 28. A slide 32 is coupled to the fixation ring 30 so as to be free to move across the fixation ring 30. The cutting head 14 is immovably coupled to the slide 32.

A plate 34, defining an applanation member, is received in the slide 32 in a predetermined fixed position. The plate 34 is operatively associated with the blade 28 to define the thickness of the resection.

In accordance with the principles of the invention, at least one sensor 36 is mounted to the automated keratome 10. In the illustrated embodiment, the sensor 36 is mounted to the plate 34. Information related to operative factors, e.g., forces the cornea itself exerts on the blade 28 in the direction of the resection, forces on the blade 28 due to the fluid dynamics of the mass of tissue flowing past the blade 28, intraoccular pressure, the pressure applied by the eyeball retaining ring on the corneal surface, speed and uniformity of translation of the keratome's cutting head, keratome blade oscillation speed, and/or other factors related to forces applied to the cornea during the cutting cycle, are routed through a feed back mechanism to intraoperatively vary one, or more, of the keratome's operating parameters. Example operating parameters for the keratome which may be intraoperatively varied are speed of traverse across the corneal surface, and/or blade oscillation speed, and/or the position of the blade 28 relative to the corneal surface.

Improvements in clinical outcomes can be achieved by incorporating sensor(s) 36 into the keratome 10 to provide feedback to the keratome's operating parameters in a manner capable of adapting performance parameters to instantaneous changes within the structure of the cornea.

A purpose of the sensor(s) 36 is to detect instantaneous changes in the response of the corneal structure to the sectioning or cutting process. Thus, suitable sensors 36 include, but are not limited to, strain gauges, piezoelectric sensors, pressure, position and speed measuring devices.

Sensors 36 can alternatively or additionally be placed in, or onto, other parts and/or surfaces of the keratome 10 in accordance with the principles of the present invention. For instance, a sensor 36' can be placed in or onto the cutting head 14 and a sensor 36" can be place in or onto the fixation ring 30 to measure forces relating to intraoccular pressure.

As noted above, one example of an improved performance automated keratome 10 utilizes a strain gauge 36 mounted within or on the applanation member or plate 34. The strain gauge 36 detects instantaneous deformation or deflection of the applanation plate 34 or member in response to variations in the forces exerted by the cornea on the blade 28 during resection as the cutting head 14 is traversing the corneal surface. A deformation signal from the strain gauge 36 is communicated to a processing unit 38 (FIG. 2), using either wired or wireless communication techniques. The processing unit 38 may include any suitable processor, e.g., microprocessor, microcontroller, or digital signal processor (DSP). The processing unit may also comprise a personal computer (PC).

Another example of an improved performance automated keratome 10 utilizes a pressure sensor as the sensor 36 configured so that the pressure sensed is via a port communicating with the applanation surface. Thus, the pressure underneath the applanation surface, which is driven by the corneal tissue, is measured and used to generate the deformation signal.

An optical encoder 40 and 44 is associated with motors 16 and 29, respectively, and processing unit 38, and are used to determine the RPM of the motors. RPM of motor 29 is used to determine oscillation speed of the blade 28 and RPM of motor 16 is used to compute the translation speed of the cutting head 14. A stepper motor may be used for the translation motor 16 to so that the absolute position of the cutting head 14 is known.

The processing unit 38 transmits a correcting signal 41 to the keratome drive motor 16 that will adjust the speed of traverse to compensate for any variation detected in the forces on the blade 28. In this way the blade force becomes the basis for controlling the speed at which the cutting head 14 traverses the corneal tissue, thus ensuring uniformity of section thickness. An algorithm can be employed to relate translation speed to flap thickness. A correcting signal 42 can also be sent to the oscillation motor 29 to control blade oscillation.

Figure 3:
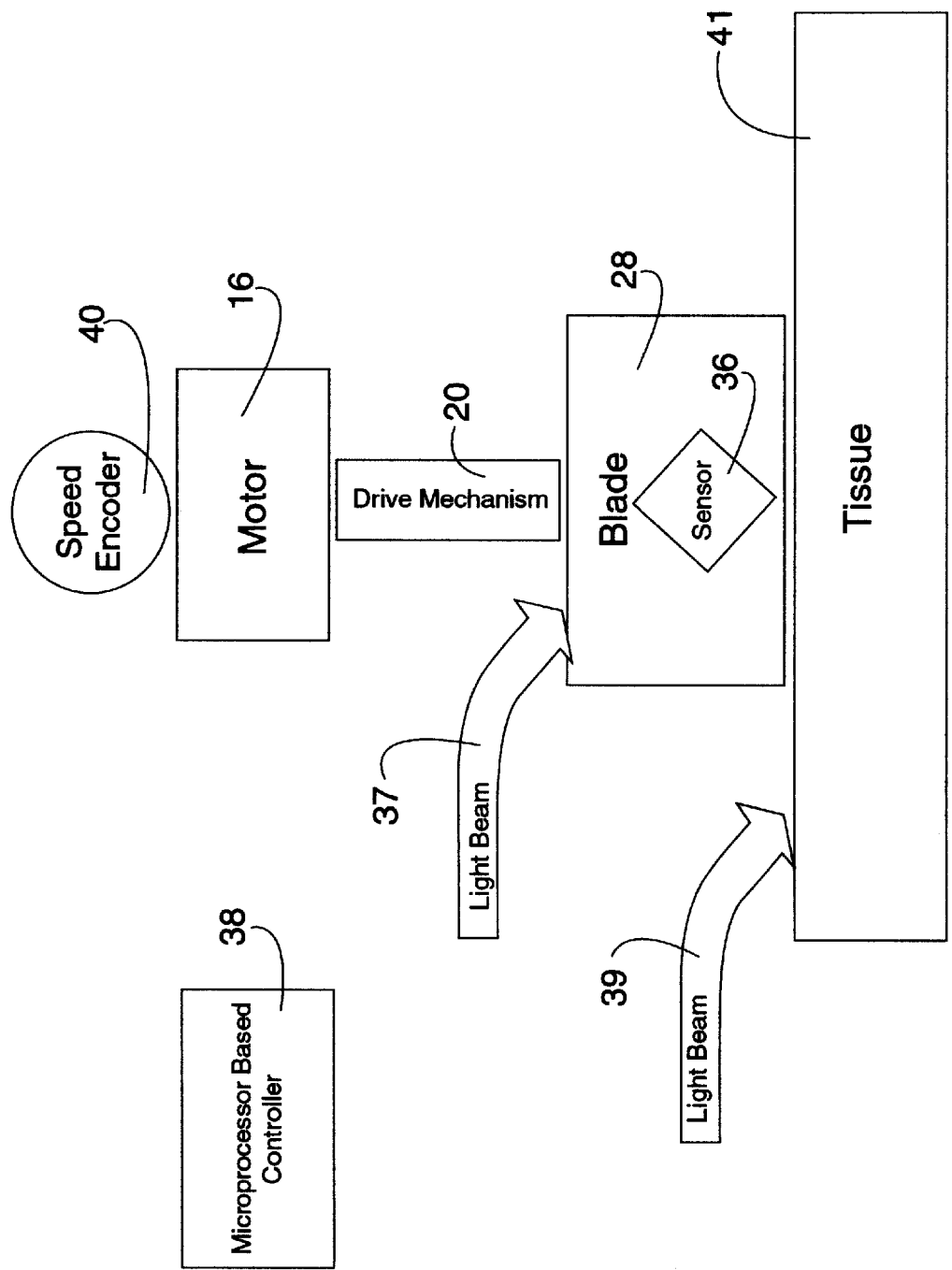
FIG. 3 is a schematic illustration of a keratome provided in accordance with another embodiment of the invention.

While motor 16 is shown in FIG. 3, another embodiment relates to manual traversal of keratome across surface of eye, while movement of the blade 28 is automated. Thus, the motor 16 may be, e.g., a handle, grip, lever, etc., allowing manual movement of the keratome across the corneal surface.

As shown in FIG. 3, the sensor 36 can measure the blade deflection directly if the sensor 36 is mounted on the blade 28. Blade deflection can be measured indirectly by optical interferometric means if the blades are configured to be disposable.

Figure 2:
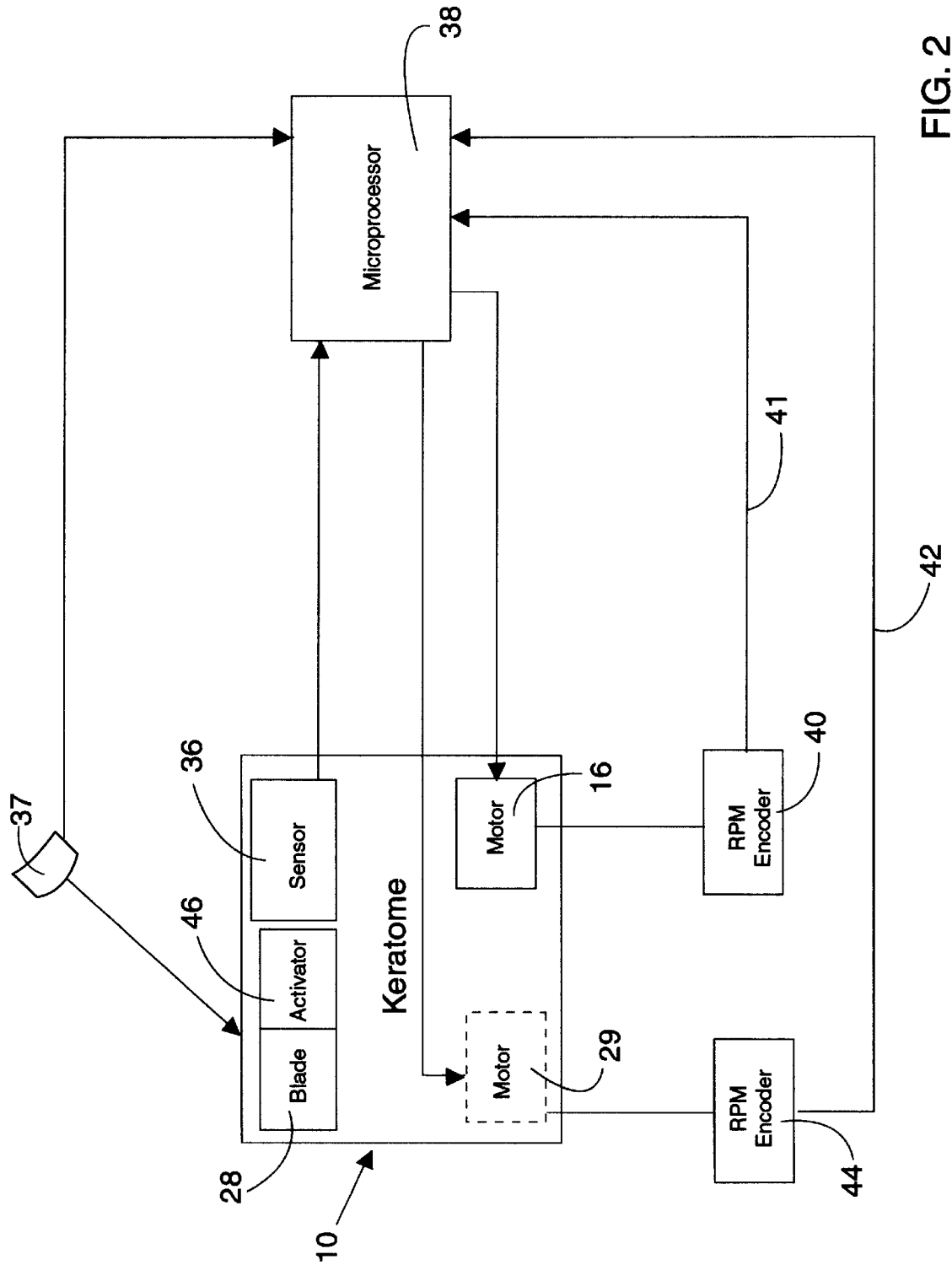
FIG. 2 is a schematic illustration of microprocessor control of the keratome of FIG. 1.

As shown in FIGS. 2 and 3, optical devices 37 and 39 are provided to measure the relative position of the blade 28 and the corneal surface. For example, the optical device 39 monitors the height of the corneal dome and the optical device 37 detects changes in the deflection of the blade 28 as it reciprocates across the tissue 41. The signal from the device 39 can be used to ensure that the tissue 41 enters the keratome 10 at a rate so as to be fed to the blade 28 at an optimum rate. Miniature actuators 46, in response to position of the blade 28 or corneal surface, move the blade 28 (or move the blade holder 26 or cutting head to thus move the blade 28) to correct the position thereof with respect to the corneal surface.

Other examples of an improved performance automated keratome in accordance with the principles of the present invention utilize signals obtained from suitable sensors placed in or on any or all of the eyeball retaining ring 30, the cutting head 14, and or the blade oscillation mechanism 24. The sensors in the eyeball retaining ring, the cutting head, and the blade oscillation mechanism detect instantaneous variations in suction pressure, speed of translation or blade position, and blade speed, respectively. Signals from these sensors form the basis for the generation of corresponding corrections to various functions of the keratome's operating parameters.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. A keratome, comprising:
    a head assembly including a cutting head and blade for cutting corneal tissue and an applanation member associated with said cutting head;
    an eyeball retaining structure; and
    a strain gauge constructed an arranged to measure deformations in said applanation member in response to forces exerted on said blade during cutting of corneal tissue, said measured deformations being used to automatically control said for forces exerted on said blade during cutting of corneal tissue.

2. A keratome, comprising:
    a head assembly including a cutting head and blade for cutting corneal tissue and an applanation member associated with said cutting head;
    an eyeball retaining structure; and
    a speed measuring device associated with said keratome providing measurement of a respective at least one operative factor during cutting of corneal tissue, said measured speed being used to automatically control said cutting of corneal tissue.

3. A keratome, comprising:
a head assembly including a cutting head and blade for cutting corneal tissue and an applanation member associated with said cutting head;
an eyeball retaining structure; and
a piezoelectric sensor associated with said keratome providing measurement of a respective at least one operative factor during cutting of corneal tissue, said at least one operative factor being used to automatically control said cutting of corneal tissue.

4. A keratome, comprising:
a head assembly including a cutting head and blade for cutting corneal tissue and an applanation member associated with said cutting head;
an eyeball retaining structure; and
at least one sensor associated with said keratome providing measurement of forces exerted on said blade during cutting of said corneal tissue, said measured forces being used to automatically control said blade during cutting of said corneal tissue.

5. A keratome, comprising:
a head assembly including a cutting head and blade for cutting corneal tissue and an applanation member associated with said cutting head;
an eyeball retaining structure;
at least one sensor associated with said keratome providing measurement of a respective at least one operative factor during cutting of cornea tissue;
a drive mechanism adapted to provide transverse movement of said cutting head across a corneal surface;
said at least one sensor is mounted to said suction ring to measure suction pressure, said measured at least one operative factor by said at least one sensor being used to automatically control said cutting of corneal tissue.

6. A keratome, comprising:
a head assembly including a cutting head and blade for cutting corneal tissue and an applanation member associated with said cutting head;
an eyeball retaining structure; and
an encoder associated with said keratome to determine RPM of said motor; and
a drive mechanism operatively associated with said motor to drive said cutting head across corneal tissue;
wherein an output from said encoder is used to automatically control operation of said cutting head across corneal tissue.

7. A keratome, comprising:
a head assembly including a cutting head and blade for cutting corneal tissue and an applanation member associated with said cutting head;
an eyeball retaining structure; and
at least one sensor associated with said keratome arranged to measure oscillation speed of said blade, an output from said at least one sensor being used to automatically control operation of said cutting head during cutting.

8. The keratome according to claim 7, wherein:
said keratome includes a motor to provide oscillatory motion to said blade, and said at least one sensor is an encoder to determine RPM of said motor.

9. A method of controlling cutting of corneal tissue with a blade of a keratome during operation, said method comprising:
measuring intraoccular pressure during operation of said keratome; and
controlling in real time a movement of the blade based on said measured intraoccular pressure.

10. A method of controlling cutting of corneal tissue with a blade of a keratome during operation, said method comprising:
measuring forces exerted on said blade during cutting of corneal tissue during operation of said keratome; and
controlling in real time a movement of the blade based on said measured forces.

11. A method of controlling cutting of corneal tissue with a blade of a keratome during operation, said method comprising:
measuring an operative factor of a keratome during operation of said keratome; and
controlling in real time translation speed of said blade based on said measured operative factor.

12. A method of controlling cutting of corneal tissue with a blade of a keratome during operation, said method comprising:
measuring an operative factor of a keratome during operation of said keratome; and
controlling in real time oscillation speed of said blade based on said measured operative factor.

13. Apparatus for controlling cutting of corneal tissue with a blade of a keratome during operation, said apparatus comprising:
means for measuring forces exerted on said blade during cutting of corneal tissue during operation of said keratome; and
means for controlling in real time a movement of the blade based on forces measured by said means for measuring.

14. A method of controlling cutting of corneal tissue using a blade of a keratome, said method comprising:
measuring instantaneous changes in a response of corneal tissue to cutting thereof during operation of said keratome; and
controlling in real time an operating parameter of said keratome based on said measured instantaneous changes.

15. A method of controlling cutting of corneal tissue using a blade of a keratome, said method comprising:
measuring intraoccular pressure during operation of the keratome; and
controlling in real time an operating parameter of said keratome based on said measured intraoccular pressure.

16. The method of controlling cutting of corneal tissue using a blade of a keratome, said method comprising:
measuring forces exerted on said blade during cutting of corneal tissue during operation of the keratome; and
controlling in real time an operating parameter of said keratome based on said measured forces.

17. A method of controlling cutting of corneal tissue using a blade of a keratome, said method comprising:
measuring an operative factor of the keratome during operation of the keratome;
controlling in real time an operating parameter of said keratome based on said measured operative factor;
sending said measured operative factor to a microprocessor; and
based on said measured operative factor, sending a signal from said microprocessor to a motor of said keratome to intraoperatively control speed of said motor.

* * * * *